US007622276B2

(12) United States Patent
Cunanan et al.

(10) Patent No.: US 7,622,276 B2
(45) Date of Patent: Nov. 24, 2009

(54) METHODS FOR PROCESSING BIOLOGICAL TISSUE (75) Inventors: Crystal M. Cunanan, Mission Viejo, CA (US); Alexandro Ochoa, Mission Viejo, CA (US); Ronald E. Cambron, Laguna Hills, CA (US)

(73) Assignee: Arbor Surgical Technologies, Inc., Irvine, CA (US)

( * ) Notice: Subject to any disclaimer, the term of this patent is extended or adjusted under 35 U.S.C. 154(b) by 0 days.

(21) Appl. No.: 11/422,576

(22) Filed: Jun. 6, 2006

(65) Prior Publication Data

US 2006/0207031 A1    Sep. 21, 2006

Related U.S. Application Data (62) Division of application No. 11/032,923, filed on Jan. 11, 2005.

(51) Int. Cl.
*G01N 1/30* (2006.01)
(52) U.S. Cl. ............... 435/40.52; 435/40.5; 435/40.51
(58) Field of Classification Search ............. 435/40.5, 435/40.51, 40.52, 40.41
See application file for complete search history.

(56) References Cited

U.S. PATENT DOCUMENTS

| | | | |
|---|---|---|---|
| 3,968,248 | A | 7/1976 | Boucher |
| 4,648,881 | A | 3/1987 | Carpentier et al. |
| 4,666,442 | A | 5/1987 | Arru et al. |
| 4,753,652 | A | 6/1988 | Langer et al. |
| 4,758,151 | A | 7/1988 | Arru et al. |
| 4,776,853 | A | 10/1988 | Klement et al. |
| 4,885,005 | A * | 12/1989 | Nashef et al. ............... 8/94.11 |
| 4,994,237 | A | 2/1991 | Login et al. |
| 5,002,566 | A | 3/1991 | Carpentier et al. |
| 5,509,932 | A | 4/1996 | Keogh et al. |
| 5,632,778 | A | 5/1997 | Goldstein |
| 5,746,775 | A | 5/1998 | Levy et al. |
| 5,843,182 | A | 12/1998 | Goldstein |
| 5,863,547 | A | 1/1999 | Miner |
| 5,891,196 | A * | 4/1999 | Lee et al. ............... 8/94.11 |
| 5,899,936 | A | 5/1999 | Goldstein |
| 5,931,969 | A | 8/1999 | Carpentier et al. |
| 5,955,353 | A * | 9/1999 | Amiot ............... 435/297.4 |
| 6,102,944 | A | 8/2000 | Huynh et al. |
| 6,193,749 | B1 | 2/2001 | Schroeder et al. |
| 6,214,054 | B1 | 4/2001 | Cunanan et al. |
| 6,334,873 | B1 * | 1/2002 | Lane et al. ............... 623/2.14 |
| 6,479,079 | B1 | 11/2002 | Pathak et al. |
| 6,509,145 | B1 | 1/2003 | Torrianni |
| 6,547,827 | B2 | 4/2003 | Carpentier et al. |
| 2002/0137024 | A1 * | 9/2002 | Cunanan et al. ............... 435/5 |
| 2003/0035843 | A1 | 2/2003 | Livesey et al. |
| 2003/0118981 | A1 | 6/2003 | Torrianni |
| 2003/0125813 | A1 * | 7/2003 | Carpentier et al. ....... 623/23.72 |
| 2003/0196274 | A1 | 10/2003 | Levy et al. |
| 2003/0226208 | A1 | 12/2003 | Carpentier et al. |
| 2003/0229394 | A1 | 12/2003 | Ogle et al. |
| 2004/0024452 | A1 | 2/2004 | Kruse et al. |
| 2004/0058444 | A1 | 3/2004 | Rajamannan |
| 2004/0093674 | A1 | 5/2004 | Cunanan et al. |

FOREIGN PATENT DOCUMENTS

| | | |
|---|---|---|
| WO | 03103739 | 12/2003 |
| WO | 2004006974 | 1/2004 |

OTHER PUBLICATIONS

Current Protocols in Molecular Biology. 1996. John Wiley & Sons, Inc. pp. A.2.1 and A.2.3.*

PCT International Search Report for PCT/US2006/000732, Applicant: Arbor Surgical Technologies, Inc., Forms PCT/ISA/210 and PCT/ISA/220, dated Jun. 12, 2007, 9 pages.

PCT Written Opinion for PCT/US2006/000732, Applicant: Arbor Surgical Technologies, Inc., Forms PCT/ISA/237, dated Jun. 12, 2007, 9 pages.

Invitation to Pay Additional Fees and Annex including Preliminary International Search for PCT/US2006/000732, Form PCT/ISA/206 and annex forms, Dated Mar. 26, 2007, 5 pages.

Cunanan, et al., Tissue Characterization and Calcification Potential of Commercial Bioprosthetic Heart Valves, Annals Thoracic Surgery, 2001; 71:S417-S421.

(Continued)

*Primary Examiner*—Leon B. Lankford
*Assistant Examiner*—Susan E. Fernandez
(74) *Attorney, Agent, or Firm*—William A. English; Vista IP Law Group LLP (57) ABSTRACT

A method for processing biological tissue used in biological prostheses includes providing a tissue procurement solution formed from a phosphate buffered saline (PBS) solution and a chelating agent. The tissue is transferred from the tissue procurement solution and undergoes chemical fixation. The fixed tissue is then immersed in a series of fresh bioburden reduction process (BRP) solutions to extract phospholipids. The tissue procurement solution reduces the bioburden on the stored tissue and preserves tissue architecture by minimizing tissue swelling. The tissue procurement solution further reduces calcium from the incoming water and/or tissue, and inhibits enzymes that digest the collagen matrix. The serial immersion of the tissue in the fresh bioburden solutions ensures optimal extraction of phospholipids thereby mitigating subsequent calcification of the tissue.

24 Claims, 10 Drawing Sheets

OTHER PUBLICATIONS

Peters, et al., Chemical Separations and Measurements, Theory and Practice of Anal. Chemistry, 1974, pp. 485-508.

ISO 14160, Sterilization of Single-Use Medical Devices Incorporating Materials of Animal Origin-Validation and Routine Control of Sterilization by Liquid Sterilants, Mar. 15, 1998.

A. Carpentier, et al., Techniques for Prevention of Calcification of Valvular Bioprostheses, Valvular Heart Disease, vol. 70 (Suppl. I), Sep. 1984.

S. Carpentier, et al., Heat Treatment mitigates Calcification of Valvular Bioprostheses, Society of Thoracic Surgeons, 1998; 66:S264-6.

S. Carpentier, et al., Biochemical Properties of Heat-Treated Valvular Bioprostheses, Annals of Thoracic Surgery, 2001; 71:S410-2.

M. Shen, et al., Effect of Ethanol and Ether in the Prevention of Calcification of Bioprostheses, Annals of Thoracic Surgery, 2001; 71:S413-6.

S. Carpentier, et al., Calcium Mitigation in Bioprosthetic Tissues by Iron Pretreatment: The Challenge of Iron Leaching, Annals of Thoracic Surgery, 1995; 60:S332-8.

European Patent Office, Office Action for European Patent Application No. 06717879.8-1219, Applicant: Arbor Surgical Technologies, Inc., Jan. 14, 2008, 5 pages.

* cited by examiner

- Sample: 0304b-9c  5/5
- Process: Full (BRP)
- Fixation Isometric
- Cut Method: Laser

FIG. 10(a)

- Sample: 0304b-10  5/6
- Process: Control (no BRP)
- Fixation Isometric
- Cut Method: Laser

FIG. 10(b)

METHODS FOR PROCESSING BIOLOGICAL TISSUE

This application is a divisional of co-pending application Ser. No. 11/032,923, filed Jan. 11, 2005.

FIELD OF THE INVENTION

The present invention relates generally to biological prostheses, and in particular, to methods for processing biological tissue that are used in biological prostheses, such as heart valves.

BACKGROUND OF THE INVENTION

Biological prostheses or "bioprostheses" are devices derived at least partially from processed biological tissues to be used for implantation into humans. Examples of bioprostheses that are currently used or in development include heart valves, vascular grafts, ligament substitutes, pericardial patches, and others. Even though much is now known about biological tissue, bioprostheses and the processing, assembly, and performance thereof, there are still deficiencies that need to be overcome to provide a bioprosthesis that preserves the native tissue properties while optimizing tissue biomechanics, minimizing calcification, and/or rendering the treated tissue hemocompatible.

For example, the biological tissue that is harvested from a donor must be stored under proper conditions, and in proper solutions, to preserve the native properties of the tissue prior to and during the tissue processing steps that are to be subsequently undertaken. In addition, the harvested biological tissue should be stored in a manner that mitigates or even reduces the bioburden of the harvested tissue.

Further, the primary component of biological tissues used to fabricate many bioprostheses is collagen, a term used here in a generic sense to refer to a family of related extracellular proteins. Collagen molecules assemble to form microfibrils, which in turn assemble into fibrils, resulting in collagen fibers. The amino acids that make up the collagen molecules contain side groups that represent sites for potential chemical reaction on these molecules. Because collagenous tissues degrade rapidly upon implantation into a host recipient, it is necessary to stabilize the tissue if it is to be used for long-term clinical applications. Chemical stabilization by cross-linking collagen molecules within the tissue (also known as tissue fixation) is well-known, and glutaraldehyde is commonly used to cross-link tissue.

Unfortunately, glutaraldehyde-fixed bioprosthetic tissues tend to become calcified over time. The mechanism by which calcification occurs in glutaraldehyde-fixed bioprosthetic tissue has not been fully explained, and many factors have been thought to influence the rate of calcification. In general, the calcification phenomenon has been characterized as being due to intrinsic causes (i.e., causes inherently contained within the tissue itself) and extrinsic causes (i.e., causes from outside the tissue itself, such as infection, patient's age, existing metabolic disorders, flow disturbances, etc.). One intrinsic cause of calcification has been shown to be the presence of phospholipids in the harvested tissues. See e.g., Cunanan et al., *Tissue characterization and calcification potential of commercial bioprosthetic heart valves*, Annals Thoracic Surgery, 2001; 71: S417-S421. Therefore, it is desirable to mitigate or inhibit the calcification of the tissue in order to increase the usable life of any bioprosthesis that is implanted into a human host.

SUMMARY OF THE INVENTION

The present invention relates to apparatus, solutions, and methods for collecting, shipping and/or processing fresh tissue, such as from the abattoir. In one embodiment, the solutions and methods may inhibit enzymatic degradation of the tissue matrix during shipment, suppresses or inhibits microbiological activity and growth prior to fixation, and/or removes background levels of calcium in the harvested tissue and water.

Furthermore, a series of solution buffers may be provided that are osmotically well-balanced and optimized to provide a greater buffering capacity and longer product shelf-life. The solutions and methods may also provide a tissue that more closely retains the native water content of pericardial tissue compared to other processes, thereby preserving the tissue's natural state prior to fixation.

In another embodiment, the tissue may be repeatedly and consecutively treated with a calcification mitigant to substantially remove calcification initiators from the tissue, thereby removing an intrinsic mechanism for calcification and reducing the possibility of early valve failure. This also may further improve the long-term durability of the resulting valve. Moreover, the tissue surface may be rendered hemocompatible during the overall process, increasing the hydrophilicity of the tissue surface compared to glutaraldehyde alone or fresh tissue.

In yet another embodiment, a solution is provided for storing biological tissue used in biological prostheses that includes a mixture of phosphate buffered saline (PBS) solution having a concentration of at least 50 mM and a chelating agent. In another embodiment, a solution for storing biological tissue used in biological prostheses includes a mixture of phosphate buffered saline (PBS) solution having a concentration of at least 100 mM and a chelating agent.

In still another embodiment, a solution is provided for storing biological tissue that is used in biological prostheses that includes a mixture of a chelating agent and a buffer selected from the group consisting of a phosphate-based buffer, a citrate-based buffer, and a borate-based buffer, the buffer having a concentration of at least 100 mM.

In yet another embodiment, a method is provided for storing harvested tissue used in biological prostheses that includes providing a solution containing a mixture of phosphate buffered saline (PBS) solution having a concentration of at least 100 mM and a chelating agent, and immersing the harvested tissue in the solution.

In another embodiment, a method is provided for processing fixed biological tissue that includes: (a) immersing the fixed biological tissue in a first fresh bioburden reduction process (BRP) solution; (b) heating the first fresh BRP solution to a temperature of about 37° C.; (c) removing the fixed biological tissue from the fresh BRP solution; (d) immersing the fixed biological tissue in a next fresh BRP solution; and (e) heating the next fresh BRP solution to a temperature of about 37° C. Optionally, steps (c), (d), and (e) may be repeated a plurality of times.

In still another embodiment, a method is provided for processing biological tissue that includes: immersing tissue in a mixture of phosphate buffered saline (PBS) solution having a concentration of at least 50 mM and a chelating agent; transferring the tissue to a phosphate buffered fixation solution; cutting a portion of the tissue into a desired shape; and transferring the cut tissue portion to a series of fresh bioburden reduction process (BRP) solutions, wherein each fresh BRP solution is heated for a period of time.

These and other aspects of the invention are described in detail below.

DETAILED DESCRIPTION OF THE INVENTION

Figure 1:
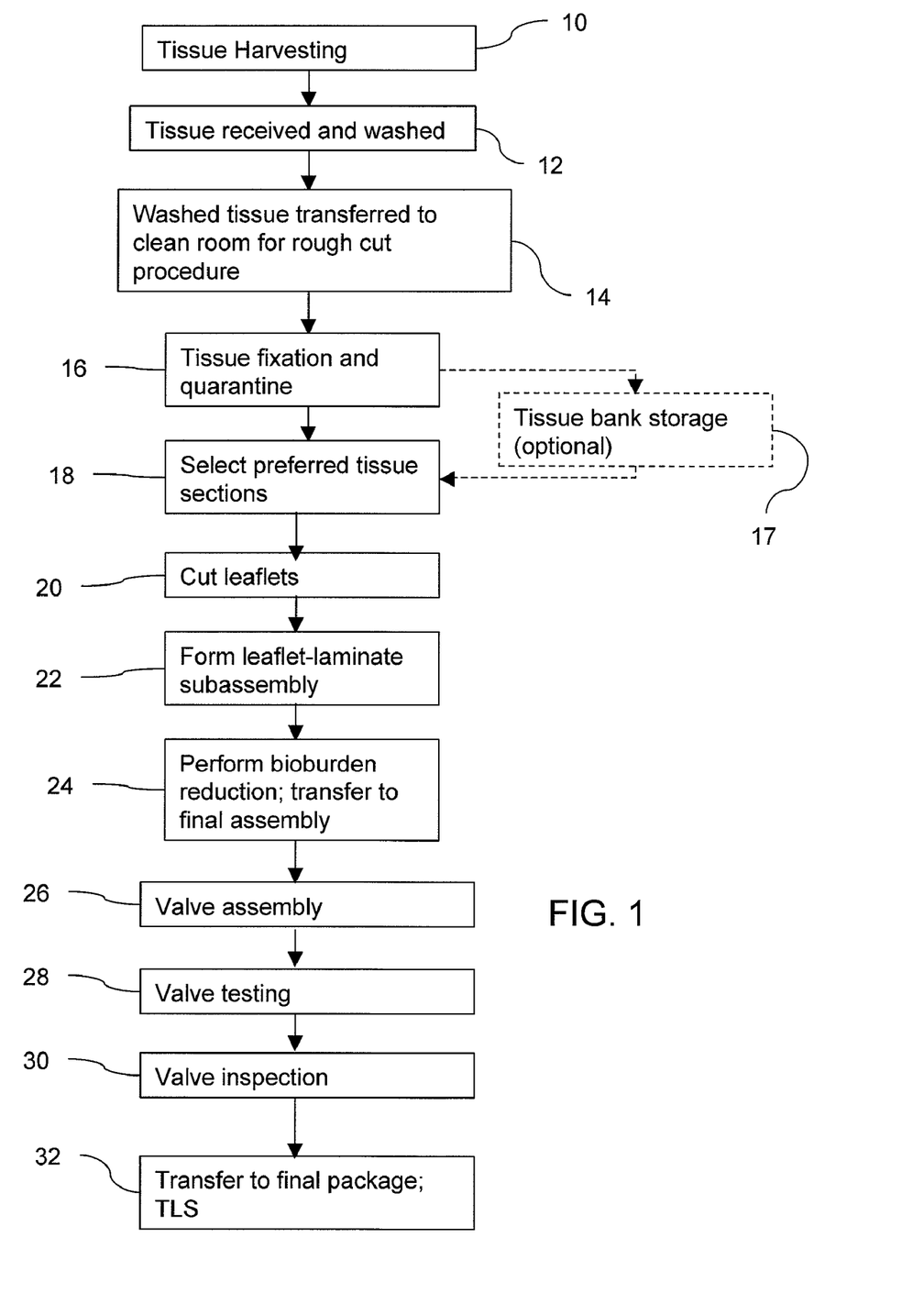
FIG. 1 is a flowchart of an exemplary tissue processing method.

FIG. 1 illustrates an exemplary method for processing tissue. Even though the method is described in connection with harvesting and processing bovine pericardium tissue used to construct heart valves, these principles may also be applied to other types of biological tissue and/or for constructing other bioprostheses. Examples of other types of biological tissue include porcine, bovine, ovine, or other aortic or pulmonary valves and vascular tissues; human donor allografts; other sources of connective tissue matrices, including porcine, equine, ovine and other xenogeneic or allogeneic pericardial tissues; dura mater; omentum or other tissues of the digestive tract; skin, placenta, uterus, or tissues reconstructed in vitro from cells from such tissues; and ocular tissues including cornea and sclera.

Examples of other bioprostheses or devices that may be formed from biological tissue processed as described herein include heart valves and valve leaflets; vascular grafts for peripheral, coronary and dialysis assess; patches, strips, or buckles used to reinforce or repair soft tissues, hard tissues, cartilage, tendon, cornea, or the like for organ repair and reinforcement for effective reconstruction procedures (including native valve reconstruction, valve annuloplasty and repair). The methods may also be applied to create structures or devices for tissue augmentation procedures (including cardiac wraps, bands, or reinforcements for congestive heart failure, vascular aneurysm repair and reinforcement including cerebral, aortic, and abdominal devices), and as an adjunct or support for other devices fabricated from synthetic materials such as DACRON or PTFE; and scaffolds for repairing and/or regenerating tissues, either before or after implantation.

With reference to FIG. 1, in step 10, the tissue is harvested at a slaughterhouse, abattoir, or the like using known techniques, and the harvested tissue is transferred to a container such as, a shipping container that contains a tissue procurement solution, such as that described further below. The shipping container is then delivered to the assembly location.

Figure 2:
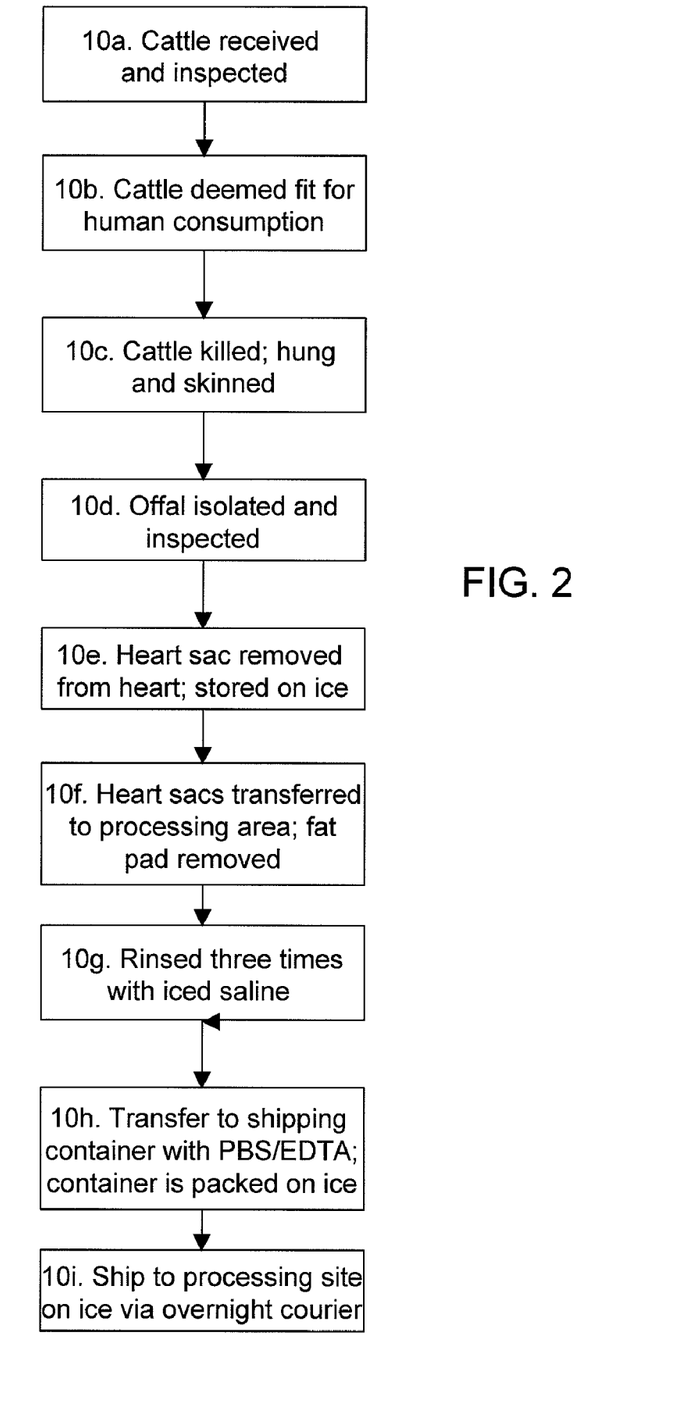
FIG. 2 is a flowchart of a tissue harvesting procedure that may be used with the tissue processing method of FIG. 1.

FIG. 2 illustrates a method for harvesting biological tissue for use in a biological prosthesis. As seen in FIG. 2, the source of tissue (e.g., bovine) is received and inspected (step 10a). Once the source of tissue is deemed suitable for human consumption (step 10b), the source is killed and is hung and skinned (step 10c). Next, the offal is isolated and inspected (step 10d). The heart sac or pericardium is removed from the heart organ and is stored on ice (step 10e). Next, in step 10f, the pericardia is then transferred to a processing area where the fat pad is removed. The processed tissue is then rinsed one or more times, e.g., three times in a rinse saline solution as indicated in step 10g. The tissue is then transferred to a shipping container or the like, e.g., containing the tissue procurement solution described in detail below (step 10h). The tissue contained in the tissue procurement solution may be packed on ice for the duration of the transfer. Finally, the shipping container is transferred from the abattoir to a processing location, e.g., via overnight courier (step 10i).

Figure 3:
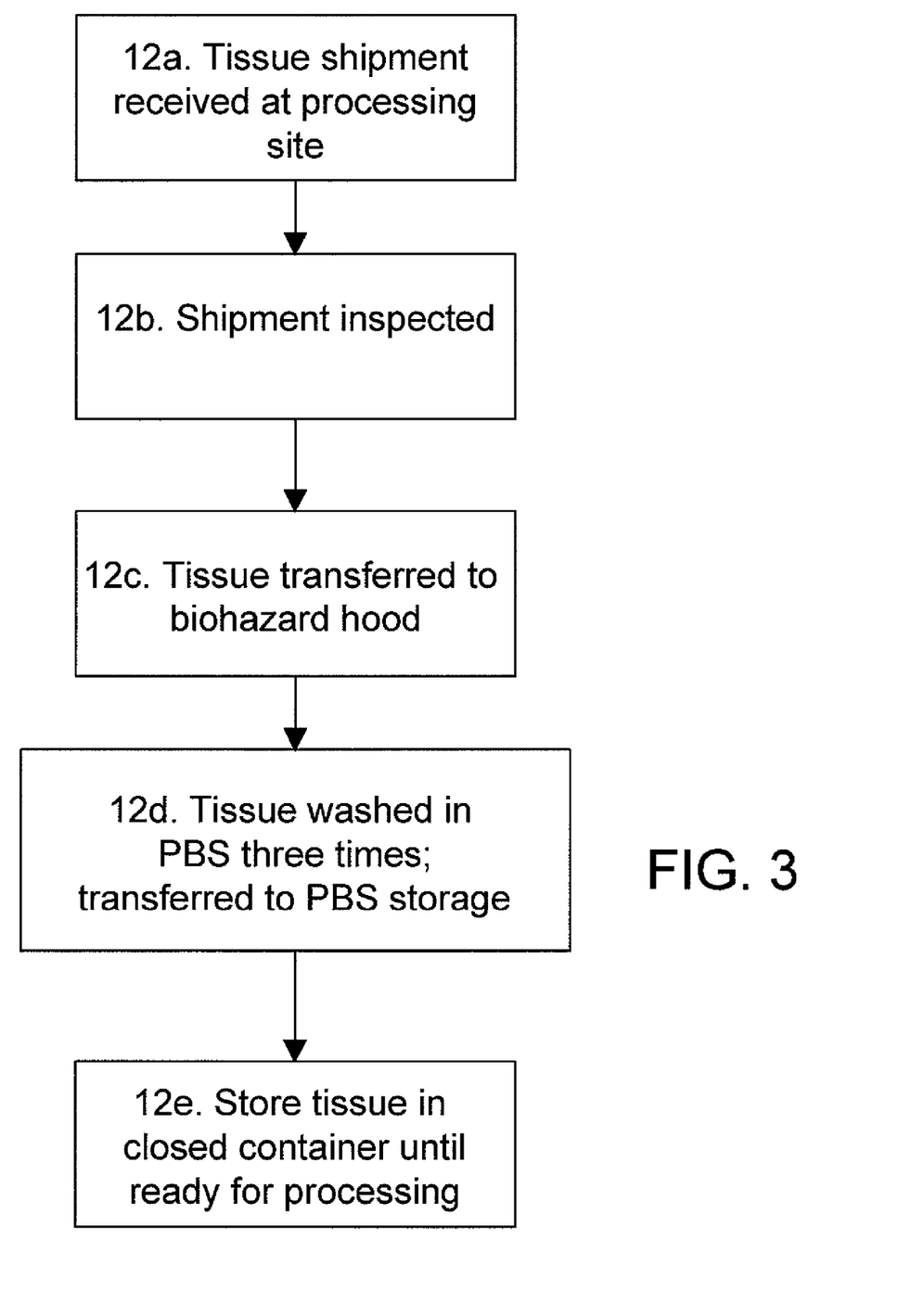
FIG. 3 is a flowchart of a process that may be used to receive harvested tissue in accordance with the tissue processing method of FIG. 1.

Referring back to FIG. 1, in step 12, the tissue is then received and washed using standard techniques. FIG. 3 illustrates one method for receiving and washing tissue. As seen in FIG. 3, in step 12a, the tissue is first received at the processing location. The shipment may be inspected in step 12b and transferred to a biohazard hood (step 12c). The tissue is then washed in PBS one or more times, e.g., three times, and is transferred to a PBS storage solution (step 12d). Finally, the tissue may be stored in a closed container until the tissue is ready for further processing (step 12e).

Figure 4:
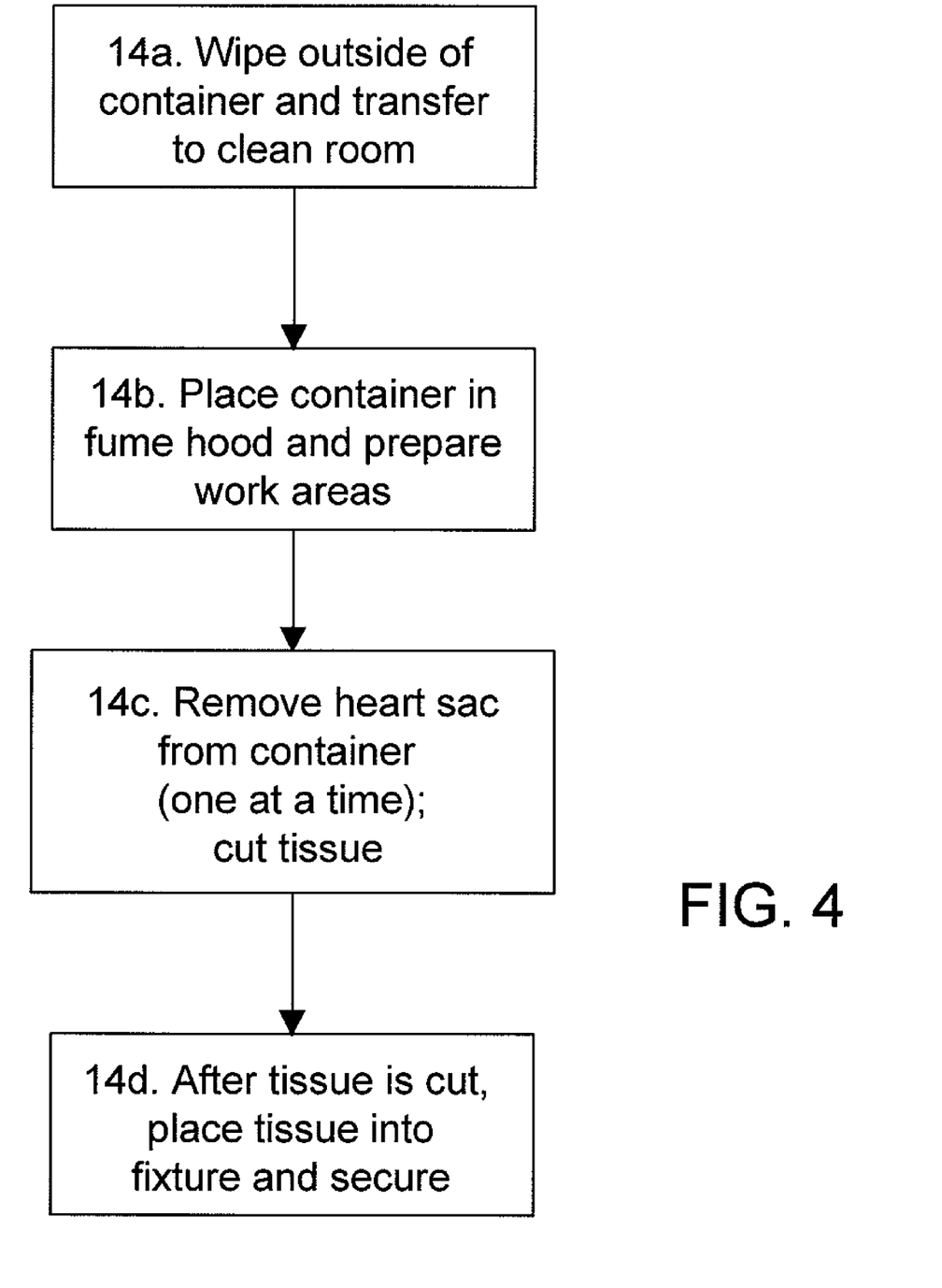
FIG. 4 is a flowchart of a process that may be used to perform a cut operation in accordance with the tissue processing method of FIG. 1.

As is seen in step 14 of FIG. 1, the washed tissue may then be transferred to a clean room for a cut procedure. FIG. 4 illustrates the steps involved in an exemplary cut procedure. As seen in step 14a in FIG. 4, the outside of the container may be wiped down and transferred to a clean room. Next, in step 14b, the container may be placed in a fume hood and the work area may be prepped. In step 14c, the pericardia is removed from the container (one at a time) and a cut is made of the tissue. Next, the cut tissue is transferred for tissue fixation (step 14d).

Referring back to FIG. 1, in step 16, the cut tissue may then be subject to tissue fixation and quarantine. First, the tissue may be hung in glutaraldehyde solution, e.g., as is described further below. After between about thirty minutes to twenty four hours exposure to the glutaraldehyde solution, the tissue may be removed from the fixation solution and placed into a storage/quarantine container, e.g., with fresh glutaraldehyde solution. The glutaraldehyde solution may be replenished periodically, for example, once every three to four days during storage/quarantine.

If desired, the tissue may be stored in a tissue bank until needed. This optional step is shown, for example, in FIG. 1 as step 17.

Figure 5:
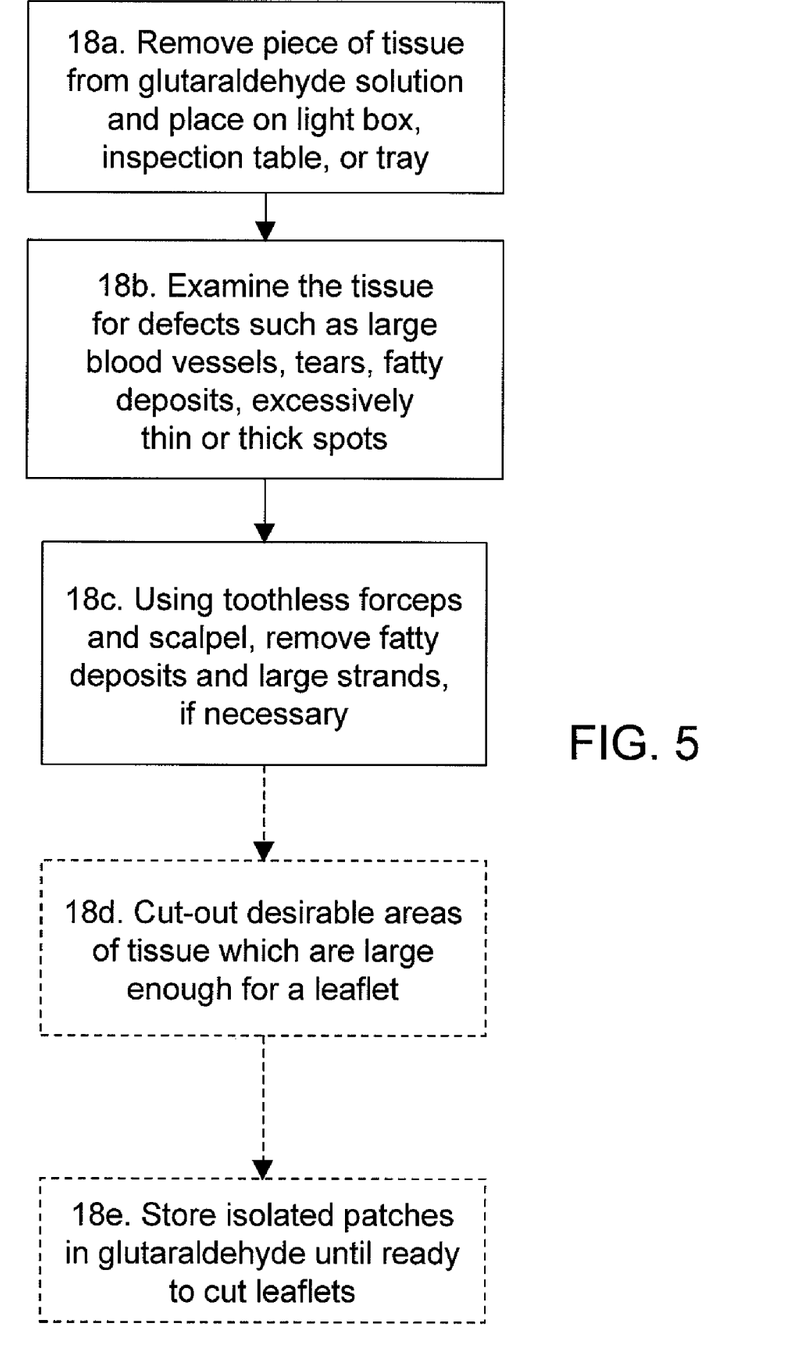
FIG. 5 is a flowchart of a process that may be used to select tissue sections in accordance with the tissue processing method of FIG. 1.

Next, in step 18 shown in FIG. 1, the good tissue sections (i.e., those tissue sections having desirable properties for a prosthetic device) may be selected, and then leaflets cut in step 20. FIG. 5 illustrates an exemplary process for selecting tissue sections. A piece of tissue may first be removed from the glutaraldehyde storage/quarantine solution and placed on a light box, inspection table, or tray (step 18a). Next, as seen in step 18b, the tissue may be examined for defects such as, large blood vessels, tears, fatty deposits, excessively thin or thick spots, and the like. Fatty deposits and large strands may then be removed using tools such as toothless forceps or curved scissors and a scalpel (step 18c). The tissue is now ready for cutting, e.g., as described with respect to step 20. Optionally, the selection step 18 may also include the additional steps of using a sterile scalpel to cut out one or more desirable areas that are large enough for a leaflet (step 18d). The cut-out areas may then be stored in a glutaraldehyde solution until the leaflets are ready to be cut (step 18e).

Referring back to FIG. 1, in step 22, sub-components of the final valve may be assembled. For example, for a bovine pericardial tri-leaflet valve, each leaflet may be stitched or otherwise attached to a laminate or frame to form one of three sub-components or leaflet sub-assemblies in step 22. The leaflet sub-assemblies may also include other components, for example, a fabric covering at least a portion of the laminate or frame, one or more connectors, and the like. As used herein, the words "sub-component" and "sub-assembly" may be used interchangeably, and have the same meaning. Additional information on leaflet sub-assemblies, and methods for making them may be found in U.S. Pat. No. 6,371,983, the entire disclosure of which is expressly incorporated by reference herein.

Figure 6:
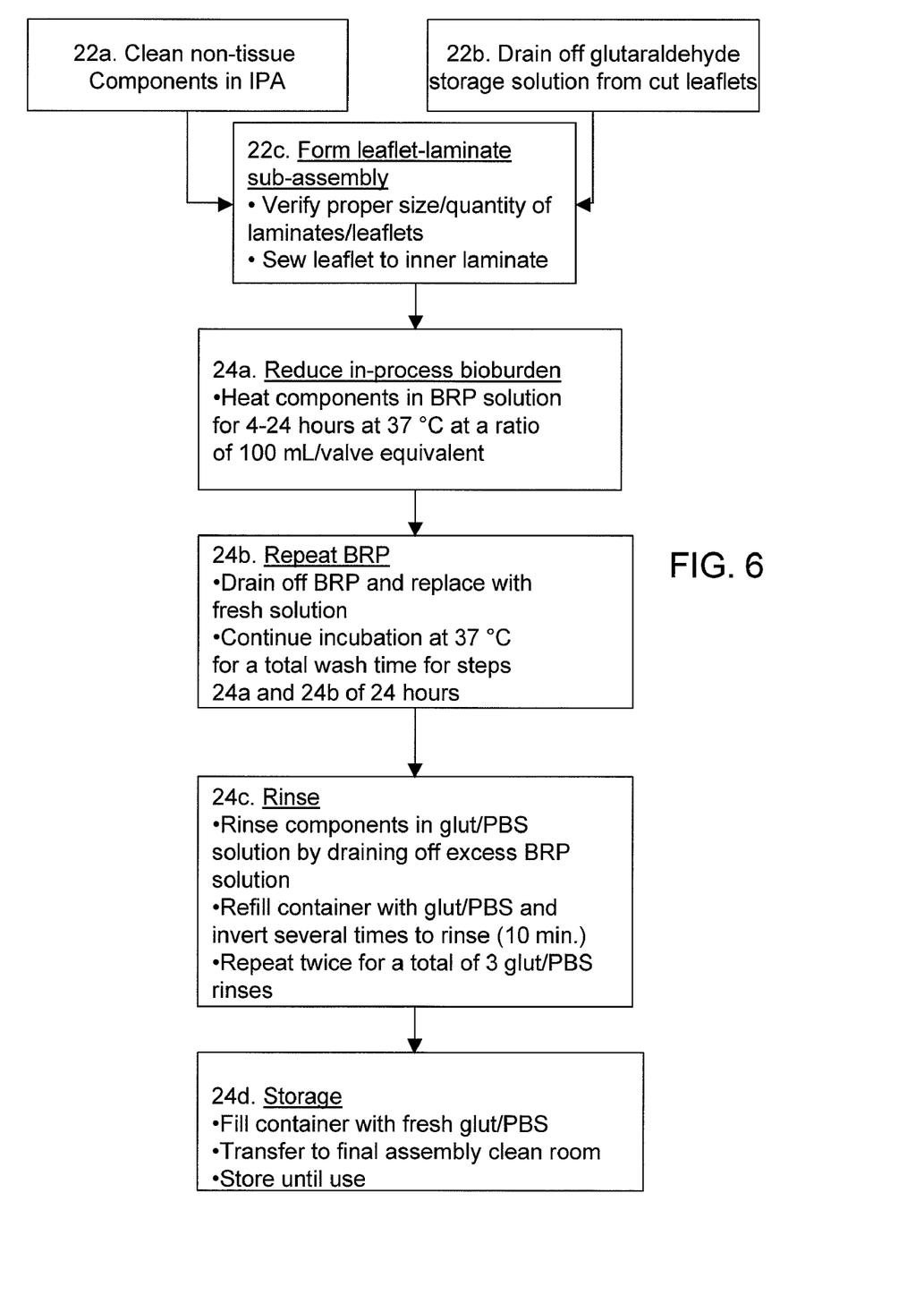
FIG. 6 is a flowchart of a process for forming leaflet-laminate sub-assemblies and reducing the in-process bioburden on them that may be used with the tissue processing method of FIG. 1.

Turning to FIG. 6, an exemplary method is shown for making one or more leaflet sub-assemblies for a valve assembly of a one-piece or multiple component heart valve prosthesis. As seen in step 22a, the non-tissue components may first be cleaned, e.g., in isopropyl alcohol (IPA). For the tissue components, the glutaraldehyde solution may be drained from the leaflets (step 22b). The leaflet sub-assembly may then be formed. As seen in FIG. 6 (step 22c), after the proper size and quantity of laminates/leaflets is confirmed, the individual leaflets are sewn to respective laminates.

With reference now to FIGS. 1 and 6, the resulting leaflet sub-assembly may then be immersed in a bioburden reduction process (BRP) solution (step 24 in FIG. 1; step 24a in FIG. 6), e.g., as described in more detail below. Generally, this involves heating the sub-assembly in the BRP solution for a period of time between about four and twenty-four (4-24) hours at a temperature of around thirty-seven degrees Celsius (37° C.), e.g., at a ratio of about one hundred milliliters per valve (100 mL/valve) equivalent. In one embodiment, the BRP solution may be drained off the leaflet sub-assembly one or more times, and the leaflet sub-assembly may be immersed in fresh BRP solution (step 24b in FIG. 6). Incubation is continued at a temperature of around 37° C. for a total wash time of about twenty-four (24) hours.

Next, the leaflet sub-assembly may be subjected to a series of rinses in a glutaraldehyde/PBS solution (step 24c in FIG. 6). After the rinse process, the leaflet sub-assembly may be transferred to a storage container, e.g., having a fresh glutaraldehyde/PBS solution therein. The leaflet sub-assembly may be stored until future use (step 24d in FIG. 6).

Figure 7:
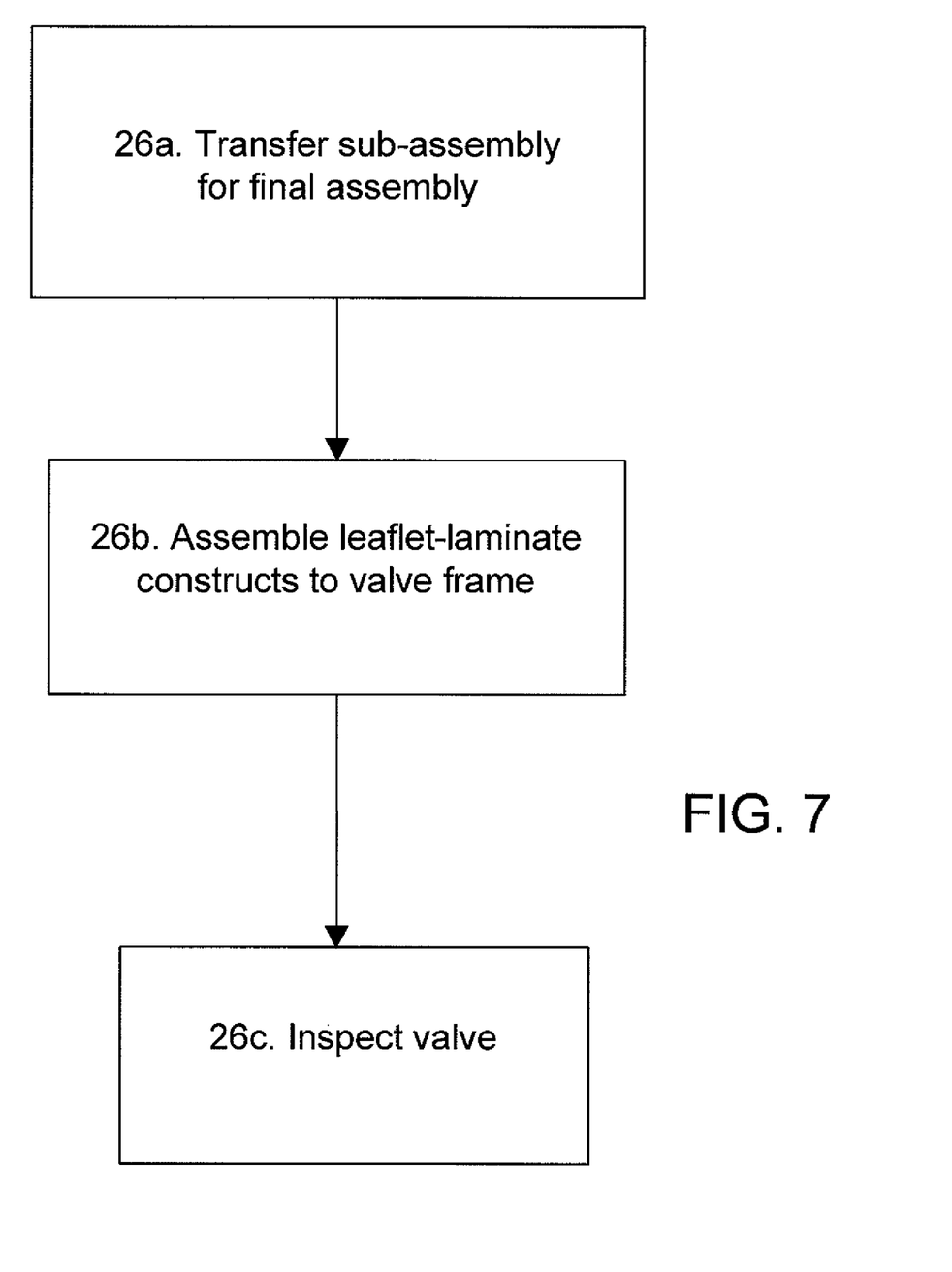
FIG. 7 is a flowchart of a process for assembling a prosthetic heart valve that may be used with the tissue processing method of FIG. 1.

Referring to FIG. 1, in step 26 the leaflet sub-assemblies may be assembled into a valve assembly (i.e., prosthetic heart valve). As seen in FIG. 7, in one embodiment, this process may include assembling the leaflet sub-assemblies to a valve frame(step 26b) and subsequently inspecting the valve assembly (step 26c).

Figure 8:
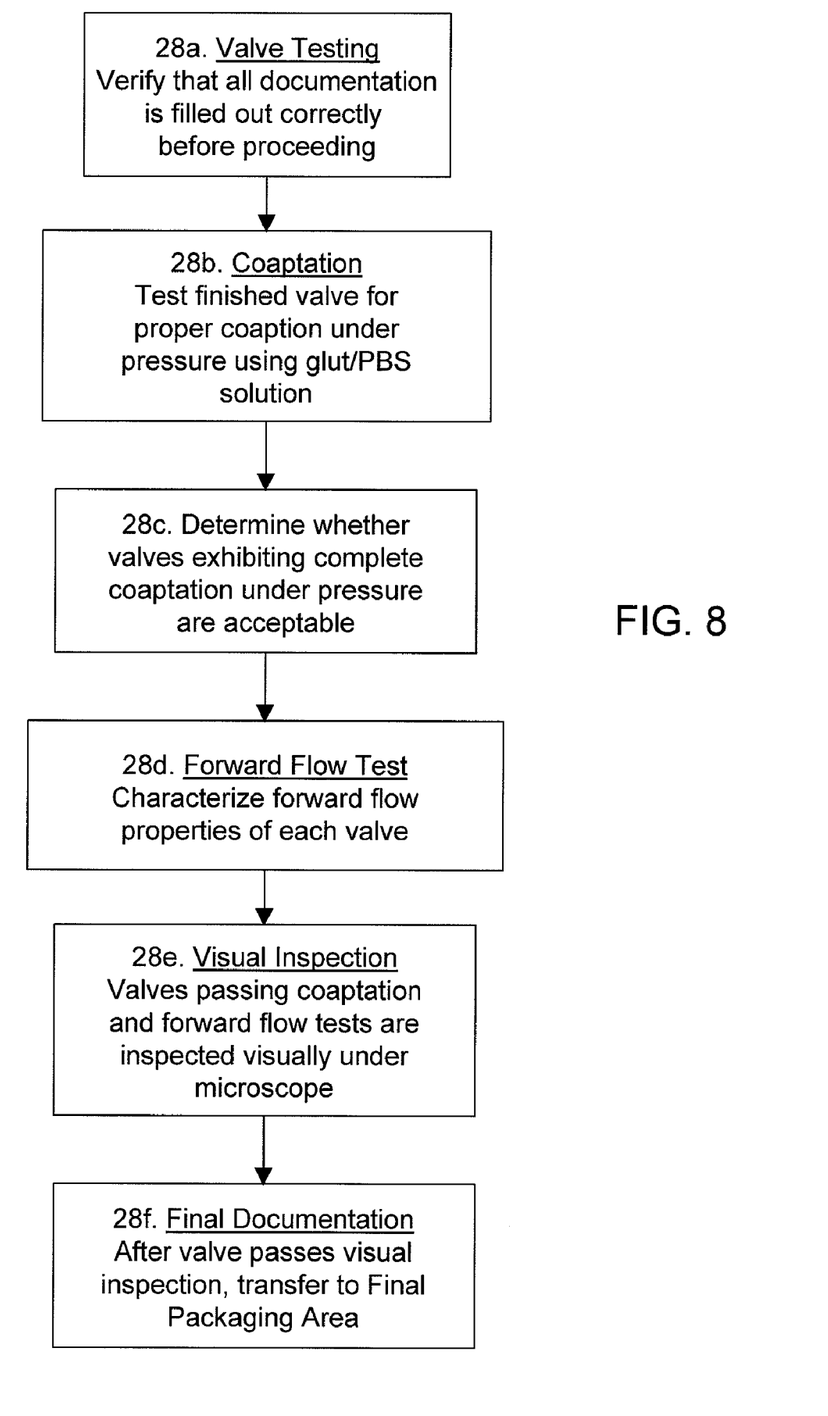
FIG. 8 is a flowchart of a process for testing a prosthetic heart valve that may be used with the tissue processing method of FIG. 1.

After assembly, the valve may be tested in step 28 using any desired testing methods. Typically, as seen in the process steps shown in FIG. 8, these tests may include coaptation tests and forward and/or backward flow tests. Tests may be performed to ensure that the assembled valves open with minimal effort, close with minimal leakage, and/or provide suitable hydrodynamic performance, e.g., at a wide range of operating flow conditions. The assembled heart valves may also be visually inspected in step 30.

Finally, in step 32, the assembled heart valves that pass the tests may be transferred to a final container where they are subjected to a terminal liquid sterilization (TLS) process before shipment to hospitals for implantation by surgeons. A technician or other qualified person may verify that the necessary documentation is complete and acceptable. The valve may then be transferred to a jar or other final container, which may be filled with a terminal sterilant. Next, a seal may be placed over the jar and sealed in place. The valve may be sterilized in the jar, e.g., by heating the jar to a desired temperature for an extended period of time. A final jar inspection may be performed to ensure the integrity of the package and any labels thereon. Finally, the valve may then be placed in storage until use.

During the various steps described herein, solutions may be used to ensure long shelf-life and/or maximal buffering capacity. These solutions may include optimal formulations that include high phosphates, including PBS-based solutions, which provide greater buffering capability, e.g., to protect the tissue against the inherent property of glutaraldehyde solutions to become more acidic with time.

For example, a tissue procurement solution may be used to store tissue after harvesting and/or before tissue fixation (i.e., after step 10 in FIG. 1). The tissue procurement solution may use an osmotically-balanced buffered salt solution, which may better preserve tissue structure and/or minimize tissue swelling. The tissue procurement solution may also include a chelating agent to chelate calcium and divalent cations. Chelating calcium may aid in removing adherent cells without damaging the tissue, may reduce calcium from the incoming water/endogenous levels in tissue, and/or may inhibit enzymes that may be released during tissue shipment or storage, which tend to digest and degrade the collagen matrix. The chelating agent may also interfere with microbial activity, thereby reducing the bioburden on the stored tissue.

In one embodiment, the tissue procurement solution may be composed of a buffering agent with a concentration of at least about 25 mM. In another embodiment, the buffering agent may have a concentration of at least about 50 mM. In yet another embodiment, the buffering agent may have a concentration of at least about 100 mM. The buffering agent may provide suitable buffering capacity around pH 6-8, or around pH 7, or within the range of pH 7.3-7.5. The buffering agent may be chemically inert with respect to glutaraldehyde reactivity, and so buffers, such as HEPES and TRIS, may be unsuitable in this application. Exemplary buffers include phosphate-based buffers, citrate-based buffers, and borate-based buffers. Phosphate buffers may be particular useful due to their ready supply, strong buffering capacity, and compatibility with downstream processing chemicals.

The solution may also contain a chelating agent, generically described as a chemical agent to complex or to bind divalent cations. It is highly desirable in the procurement of fresh tissues to inhibit the action of proteolytic enzymes before preserving the tissue by fixation techniques, and the binding of divalent cations "stops" or otherwise inhibits the action of many enzymes that require divalent cations in the active site for proteolysis. Divalent cations are also essential for basic cellular functions, such as adhesion and cell division, so chelation of divalent cations may also be an effective way to remove adherent cell layers with minimal handling. Bacterial cells may also be inhibited by the chelation of divalent cations, so that the use of chelating agents in the procurement solution of fresh tissues may aid in bacteriostasis.

Figure 9:
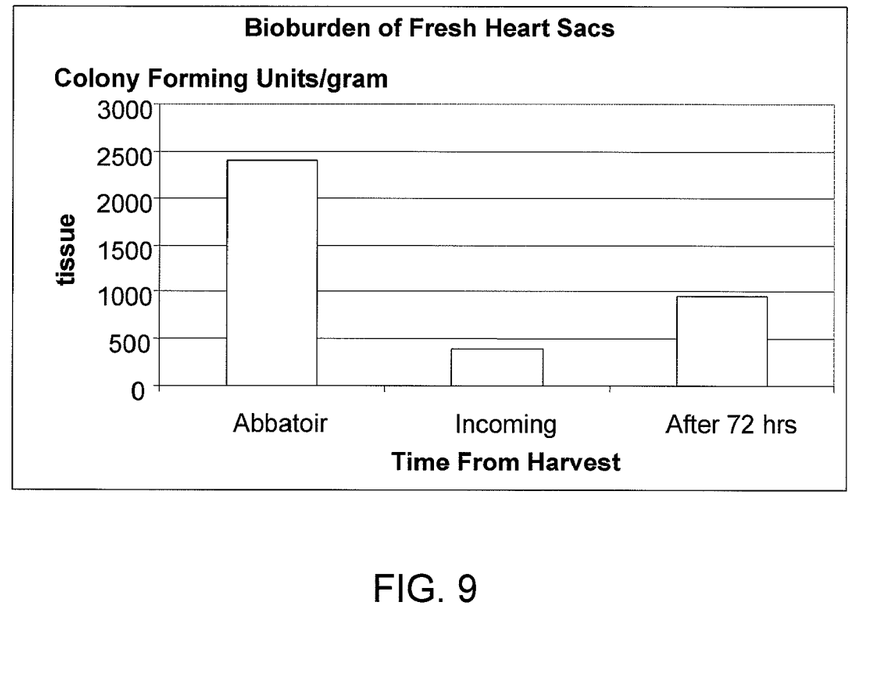
FIG. 9 illustrates reduction in bioburden levels in tissue that has been stored in a tissue procurement solution prepared as described herein.

It has been found that the tissue procurement solution has the ability to maintain or even reduce the bioburden on harvested tissue. FIG. 9, for example, illustrates the reduction in bioburden levels in tissue that has been stored in the above-described tissue procurement solution. Finally, with respect to the chelating aspect of the tissue procurement solution, by chelating divalent cations, including divalent cations such as calcium ions, the overall calcium load in tissue may be reduced, both from the tissue itself and from processing chemicals and water.

Suitable chelating agents that may be used in the tissue procurement solution include well-known aminopolycarboxylic acids, such as EDTA (ethylenediaminetetraacetic acid) and EGTA (bisaminoethyl-glycolethertetraacetic acid), as well as polymeric ether chelating agents such as the polyoxyethylenes, polyoxyglycols, and poly-glymes; other structural components which form similar shapes such as cyclic antibiotics, amino acid peptides, and wholly synthetic or biological compounds, such as modified fullerenes, dendrimers, polysaccharides, polynucleic acids, or other compounds capable of complexing divalent cations due to their three dimensional shape and ionic character. The principal action of the agents described is complexation of metal compounds, such as calcium and magnesium, through one or more electron-donating groups. Metal cations have several available orbitals for bond formation with complexing agents; therefore, the chelating agent can be monodentate (from the Latin word dentatus, meaning "toothed."), such as the chlorides, cyanides, hydroxides, or ammonia complexes, and mixed complexes may be formed from these. In addition, the ligand may be multidentate, or containing multiple teeth, which can contribute two or more electron pairs to a complex. Ethylenediamine, $NH_2CH_2CH_2NH_2$, is an exemplary bidentate ligand. Other useful members of the aminopolycarboxylic acid family include DCTA (trans-diaminocyclohexanetetraacetic acid), NTA (nitrilotriacetic acid), and DTPA (diethylenetriameinepentaacetic acid).

In one embodiment, the tissue procurement solution may be delivered or otherwise formed on-site in concentrate form that may be subsequently diluted, e.g., before tissue submersion. Table 1 below illustrates an example of a solution of a PBS-EDTA tissue procurement solution. After dilution to one liter (1.0 L), the tissue procurement solution has a pH within the range of about 7.3 to 7.5. The final pH of the solution may be adjusted with either 1N hydrochloric acid (HCl) or 1N sodium hydroxide (NaOH) on an as-needed basis. In addition, post-dilution, the tissue procurement solution may have an osmolarity level within the range of about 290-310 mOsm or around 300 mOsm.

TABLE 1

| Chemical | Specification |
| --- | --- |
| Sodium Chloride (NaCl) | 20.4 ± 0.1 g |
| Potassium Phosphate Monobasic ($KH_2PO_4$) | 20.0 ± 0.1 g |
| Sodium Phosphate Dibasic heptahydrate ($Na_2HPO_4 \cdot 7H_2O$) | 230 ± 0.1 g |
| EDTA | 25.0 ± 0.1 g |
| Hydrochloric Acid (HCl) | As needed |
| Sodium Hydroxide (NaOH) | As needed |
| Purified Water | Dilute to 1.0 L |

Tissue stored in the tissue procurement solution described above may be removed and subjected to a fixation process (i.e., step 16 in FIG. 1). In one embodiment, the fixation method involves the application of a directional force on a piece of tissue during the fixation process. The methods and apparatus disclosed in Lee et al., *The Bovine Pericardial Xenograft: III. Effect of Uniaxial and Sequential Biaxial Stress During Fixation on the Tensile Viscoelastic Properties of Bovine Pericardium*, Journal of Biomedical Materials Research, Vol. 23, 491,-506 (1989) may be used to apply the directional force. The above-identified Lee et al. publication is expressly incorporated by reference as if set forth herein.

In an alternative embodiment, the tissue strips may be pre-conditioned in a phosphate-buffered saline (PBS) solution for about thirty minutes at room temperature. Pre-conditioning may be desired in processes that seek minimal tissue fixation durations and/or utilize tissues that are not easily aligned with a directional force. In such cases, pre-conditioning enables a relaxation of the tissue component architecture under the directional force before application of fixation chemicals, and may be enhanced with suitable time, temperature, and/or variable weights.

The fixation solution may be a glutaraldehyde solution or any other known fixation solution. In one embodiment, the fixation solution may include between about 0.50% and 0.65% glutaraldehyde (on a volume basis) in PBS. In another embodiment, the fixation solution may include about 0.57% glutaraldehyde (on a volume basis) in PBS buffer. Table 2 below illustrates an example of a 0.57% glutaraldehyde solution. After dilution to one liter (1.0 L), the solution has a pH within the range of about 7.3 to 7.5. The final pH of the solution may be adjusted with either 1N hydrochloric acid (HCl) or 1N sodium hydroxide (NaOH) on an as needed basis. In addition, post-dilution, the tissue procurement solution has an osmolarity level within the range of about 290-310 mOsm or around 300 mOsm.

TABLE 2

| Chemical | Specification |
| --- | --- |
| Sodium Chloride (NaCl) | 0.96 (as needed) |
| Potassium Phosphate Monobasic ($KH_2PO_4$) | 2.00 ± 0.02 g |
| Sodium Phosphate Dibasic heptahydrate ($Na_2HPO_4 \cdot 7H_2O$) | 20.57 ± 0.02 g |
| 24% Glutaraldehyde | 23.75 ± 0.1 ml |
| Hydrochloric Acid, 1N (HCl) | As needed |
| Sodium Hydroxide, 1N (NaOH) | As needed |
| Purified Water | Dilute to 1.0 L |

After fixation, the tissue is then placed into a glutaraldehyde solution for quarantine/storage. For example, the tissue strip may be laid flat, e.g., with the smooth side facing upwards, in a covered sterile holding tray that is filled with sterile filtered 0.57% glutaraldehyde and PBS. This glutaraldehyde solution may be replenished periodically (e.g., every three to four (3-4) days) during quarantine. Quarantine is the period of time that allows the fixation reaction to go substantially to completion. After the fixation quarantine time is substantially complete, tissues may be stored for long periods of time, e.g., until needed, particularly if the tissues are refrigerated, for example, stored in a liquid media at a temperature within the range of about two to twelve degrees Celsius (2-12° C.) or similar chilled conditions.

Optionally, as an alternative to the application of a uniaxial (one-directional) force, it is also possible to apply a biaxial (two-directions) or an isometric (all directions) force by positioning weight(s) at the desired portions of the tissue strip.

During the process of fixation, application of a force in a longitudinal direction along the length of the tissue is believed to align the collagen molecules during fixation with crosslinking agents, such as glutaraldehyde. The tissue is suspended in crosslinking solution, with one end fixed to a holder, and the other end left free with a hanging weight. Applying a biasing force to the tissue during fixation may also produce more uniform tissue by stretching out some of the intrinsic variability from piece to piece, which may facilitate manufacturing by creating substantially uniform tissues with predictable properties. Thus, this fixation method may enable the engineering of tissue with specific biomechanical properties, while substantially reducing tissue-to-tissue variability.

After the fixation process, tissue sections may be selected and cut into one or more desired shapes or geometries, e.g., by die-cutting or laser cutting. In the case of prosthetic heart valves, the tissue may be cut into leaflets.

The solutions and procedures described herein may provide a post-fixation method that mitigates or inhibits calcification of tissue. An exemplary post-fixation treatment method involves repeatedly immersing the fixed tissue in a series of fresh bioburden reduction process (BRP) solutions to effect more complete extraction of phospholipids. This method may be applied to tissue alone, or, as shown in step 24 of FIG. 1, to the tissue and its non biological components, e.g., leaflet sub-assemblies.

In one embodiment, the BRP solution may be a glutaraldehyde and polysorbate-80 solution (i.e., TWEEN-80), such as that described in U.S. Pat. No. 4,885,005 (Nashef et al.), the entire disclosure of which is expressly incorporated by this reference herein. For example, the BRP solution may be an aldehyde-polysorbate-80 solution, e.g., as described in Example V of U.S. Pat. No. 4,885,005 (Nashef et al.).

Table 3 below illustrates an exemplary BRP solution. After dilution to one liter (1.0 L), the BRP solution has a pH within the range of about 7.3 to 7.5. The final pH of the solution may be adjusted with either 1N hydrochloric acid (HCl) or 1N sodium hydroxide (NaOH) on an as needed basis.

TABLE 3

| Chemical | Specification |
| --- | --- |
| Sodium Chloride (NaCl) | 2.00 g |
| Potassium Phosphate Monobasic (KH$_2$PO$_4$) | 2.24 g |
| Sodium Phosphate Dibasic heptahydrate (Na$_2$HPO$_4$•7H$_2$O) | 23.54 g |
| 24% Glutaraldehyde | 41.67 ml |
| Polysorbate 80 (Polyoxyethylene Sorbitan Monoleate; polysorbate-80) | 20.0 ml |
| Hydrochloric Acid, 1N (HCl) | As needed |
| Sodium Hydroxide, 1N (NaOH) | As needed |
| Purified Water | Dilute to 1.0 L |

According to one post-fixation method (see FIG. 6), the tissue may be placed in a first container that contains the BRP solution. The container may be a jar or other vessel, and the tissue may be placed into the BRP solution retained therein. If the tissue has been assembled into a sub-component, e.g., as in step 22 of FIG. 1, then the entire sub-component (e.g., tissue, laminate, cloth, etc.) may be placed in the BRP solution inside the container.

Next, in step 24*a*, the container (with the tissue or sub-component immersed within the BRP solution therein) may be heated for a period of time at a desired temperature, e.g., of about thirty-seven degrees Celsius (37° C.±2° C.). The container, and consequently, the BRP solution, may be heated for a period of time between about four and sixteen (4-16) hours. Next, as seen in step 24*b*, the tissue or sub-component is then removed from the container, and immediately placed into a second container that contains a fresh BRP solution. This second container may then be heated for a period of time at a temperature, e.g., also of about thirty-seven degrees Celsius (37° C.±2° C.). Again, the BRP solution may be heated for a period of time, e.g. between about four and sixteen (4-16) hours. Optionally, the first container may be reused as the second container (as long as the first container is refilled with a fresh BRP solution).

The above described process may be repeated one or more times in a plurality of fresh BRP solutions. Generally, the process may be repeated with any number of fresh BRP solution changes, as long as the total time the tissue is heated at the desired temperature is at least about one (1) hour. While there is no apparent upper limit to this exposure process, from the practical aspects of the process, it may be desirable to limit the overall BRP exposure to about twenty four (24) hours. As an example, the tissue or sub-component may be heated at the desired temperature, e.g., about 37° C. (±2° C.), in a first fresh BRP solution for about four (4) hours, in a second fresh BRP solution for about six (6) hours, in a third fresh BRP solution for about four (4) hours, and in a fourth fresh BRP solution for about six (6) hours (total of about twenty hours (20) exposure). The effective driving force for the extraction process is the physicochemical partitioning of the phospholipids between the tissue phase and the soluble phase (i.e., BRP solution). Thus, performing the extraction process at least twice, immediately after the other, is the key to efficiently removing the phospholipids. The process and rate of removal of phospholipids is affected by several variables including time, temperature, pressure, and/or concentration, and one skilled in the art will know how to optimize these variables in order to effect optimal extraction.

In an alternative embodiment, the phospholipids may be extracted using a co-current, cross-current, or counter-current separation system wherein the phospholipids may be substantially continuously extracted with fresh BRP solution for maximum extraction efficiency. Such a process may use any combination of time, temperature, concentration, and/or pressure, provided those conditions do not adversely affect the tissue properties. In such an instance, automation and solvent exchange/delivery systems may provide manufacturing advantages to help realize the effectiveness of the concept of repeated extractions in removing phospholipids from tissue to mitigate or reduce calcification.

One skilled in the art will also realize that the composition of the BRP solution may be varied to include a variety of compounds, as long as the phospholipids are soluble in it. Therefore, while detergents such as polysorbate-80 are useful, other phospholipid-solvating compounds may be effective, provided they contain both a polar component and a non-polar component. It is desirable that the polar component be neutral, rather than an ionic component. While compounds such as polysorbate-80 contain these functions within the same molecule (known as amphiphilic), mixtures of simple chemicals may achieve the same purpose. For example, mixtures of alcohols with nonpolar compounds (such as ethers, chloroform, or other nonpolar solvents) may be effective; in the case of water as the polar compound, alcohols may provide the nonpolar functionality of the solution, provided the molecular weight and concentration of the alcohol in the water are sufficiently high. For example, methanol-water mixtures may not be effective solvents for removing phospholipids in tissues, but ethanol-water mixtures may be used. Generally, the methods described herein contemplate using a detergent or phospholipid-solvating solution comprising multiple solvents having a wide range of polarities. Temperature, time, pressure, and/or other conditions may again be altered to optimize the removal of phospholipids. In this particular case, a buffered glutaraldehyde based solution (PBS buffer system) may be particularly useful in order to provide microbiocidal activity while preserving tissue structure (physiologic osmolality, pH, etc.). If, however, it is not desirable or necessary to retain microbiocidal activity and/or preserve tissue structure, significantly more leeway may be applied in the choice of the polar/non-polar system used in the extraction and in the precise extraction conditions. In particular, processes used to make tissues not performing significant mechanical functions (soft tissue augmentation and repair, ocular tissues, etc.) may employ a wide range of conditions in order to accomplish the goals described herein.

After the repeated changes in step 24b, the tissue or sub-component may be rinsed in step 24c. First, the final BRP solution may be drained from the container, and the container filled with a solution, e.g., containing 0.57% glutaraldehyde and PBS (see above). The tissue or sub-component may be placed into the glutaraldehyde and PBS solution and allowed to sit at a desired temperature, e.g., room temperature, for a desired period of time, e.g., approximately five to ten (5-10) minutes. The container may then be inverted to rinse the tissue or sub-component. This rinsing may be repeated two or more times with two fresh glutaraldehyde and PBS solutions, e.g., for a total of three rinses.

After post-fixation treatment, the tissue or sub-component may be stored in a terminal sterilant solution. In one embodiment, the terminal sterilant solution may have anti-microbial properties as well as a strong buffering capacity to ensure longer shelf life. For example, a terminal sterilant solution compliant with International Standard ISO 14160 may be used, the entire disclosure of which is expressly incorporated by reference herein.

EXAMPLE 1

Bovine pericardium tissue samples were subject to the processing steps described in detail herein. In addition, control samples ("glut only") were subject to the same processing steps with the exception of the bioburden reduction process and terminal sterilization process. For the control samples, the tissue samples were incubated at 32° C. with a 0.57% glutaraldehyde solution.

Samples of bovine pericardium were obtained and stored in a tissue procurement solution (PBS/EDTA solution) prior to arrival. Initial tissue samples were first rinsed in PBS and fat deposits were removed. The tissue samples were then subject to either uniaxial fixation or isometric fixation. For uniaxial fixation, the tissue was cut into 60×160 cm rectangular strips. One end of the tissue (upper end having a width of 60 cm) was secured to a dialysis clip. A stainless steel rod (weighing about 35-40 g) was placed on the opposing lower end of the tissue strip. The tissue was folded over the rod and secured in place with a dialysis clip.

A 1000 ml beaker was filled almost to the brim with a 0.57% glutaraldehyde solution. Two stainless steel spatulas were placed in parallel over the top of the beaker. The weight and dialysis clip were then lowered into the beaker, using the spatulas as a support for the dialysis clip located on the upper end of the tissue. The tissue sample was allowed to hang immersed in the fixation solution for a minimum of thirty (30) minutes. After fixation, the tissue clips were removed from the sample and the tissue was placed in a storage container filled with 0.57% glutaraldehyde solution.

For isometric fixation, bovine pericardium tissue was cut into a 11 cm square and placed over the edge of an isometric pressure fixture. The top of the pressure fixture is circular in shape and has a diameter of about 10 cm. The tissue was fixed to the pressure fixture using a zip tie. A constant flow rate of 0.57% glutaraldehyde solution was then pumped on the top of the tissue. A hole located about one-quarter inch above the upper surface of the tissue kept the glutaraldehyde level constant during the immersion step.

After fixation, the tissue was cut into either 1×4 cm strips or 10 mm disks. The rectangular strips were cut using a scalpel while the disk-shaped samples were formed using either a laser or a conventional die cutting process. The cut samples where then subject to a bioburden reduction process. Control samples were not subject to the bioburden reduction process. For non-control tissue samples, the tissue was placed in 100 ml jars filled with a bioburden reduction process (BRP) solution of the type described herein and incubated at 37° C. for sixteen (16) hours. Samples were then removed from the incubator, and the BRP solution was decanted and replaced with fresh BRP solution. The samples continued to incubate at 37° C. for a total of twenty-four (24) hours.

After the incubation period was complete, the jars containing the tissue samples were rinsed three times using a 0.57% glutaraldehyde solution for a period of ten minutes each. A three hour soak of the tissue samples in 0.57% glutaraldehyde solution followed the rinse steps. After the soak operation, the glutaraldehyde solution was decanted and replaced with fresh 0.57% glutaraldehyde solution. The samples were stored in this solution at room temperature until ready for the final sterilization step.

For final sterilization, the tissue samples were removed from the storage jar and placed into a clean, autoclaved jar. The jar was then filled with a terminal sterilant and the jar was closed using a new sterile lid. The jar was then vacuum tested for any leaks. Once the jar was sealed and no leaks were identified, the jar was placed upright into a 32° C. incubator for forty-eight hours.

Figure 10A:
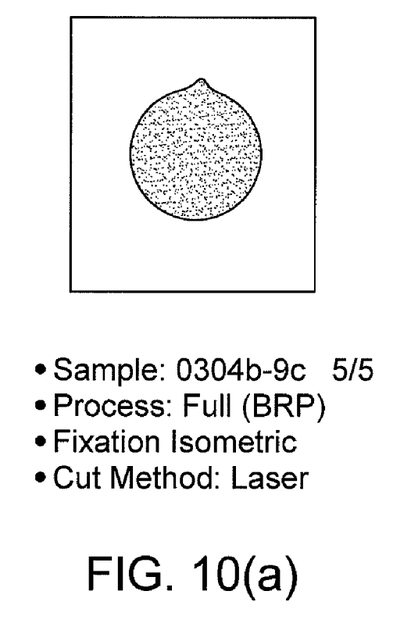
FIG. 10(a) illustrates a radiograph of a sample of fixed tissue that has undergone processing as described herein.
Figure 10B:
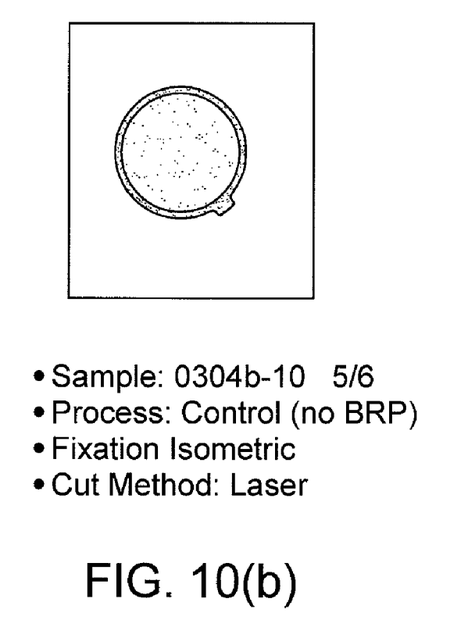
FIG. 10(b) illustrates a radiograph of a control sample of fixed tissue (no BRP—glutaraldehyde only).

The tissue samples (including controls) were then implanted subcutaneously in rats. After twenty-one days, the rats were killed and the tissue was excised and placed in 10% formalin solution. The host tissue was then removed and the tissue samples were rinsed and dried. The tissue samples were examined for moisture content as well as for calcium and phosphorous content. Radiograph images were taken of the samples for analysis of calcium levels. Radiograph photographs indicated that the "glut only" control samples had higher calcium levels than both the strip and disk tissue samples (based on denser appearance of control radiographs). FIG. 10(*a*) illustrates a radiograph of a sample of isometrically fixed tissue that underwent processing according to the present invention. FIG. 10(*b*) illustrates a radiograph of a control sample of isometrically fixed tissue (no BRP—glutaraldehyde only).

Table 4 below illustrates the measured calcium and phosphorous levels for tissue samples subject to isometric fixation. Calcification and phosphorous analysis was performed using Inductively Coupled Plasma—Optical Emission Spectroscopy (ICP-OES). As seen in the Table 4, the control samples showed an average calcium level of 117 μg/mg while the tissue samples subject to the bioreduction process showed an average calcium level of 0.41 μg/mg.

TABLE 4

| Arbor Sample Number | Sample Shape | Calcium | Phosphorus | Process | Fixation Method | Cutting Method |
| --- | --- | --- | --- | --- | --- | --- |

TABLE 4-continued

| | | | | | | |
|---|---|---|---|---|---|---|
| 0304b-1 | Disk | 100 | 42 | Control | Uniaxial | Scalpel |
| 0304b-1 | Disk | 116 | 46 | Control | Uniaxial | Scalpel |
| 0304b-3 | Disk | 0.38 | 2.8 | BRP | Uniaxial | Scalpel |
| 0304b-3 | Disk | 0.18 | 2.5 | BRP | Uniaxial | Scalpel |
| 0304b-3 | Strip | 0.74 | 2.9 | BRP | Uniaxial | Scalpel |
| 0304b-2 | Disk | 113 | 53 | Control | Uniaxial | Scalpel |
| 0304b-2 | Disk | 113 | 58 | Control | Uniaxial | Scalpel |
| 0304b-2 | Strip | 58 | 32 | Control | Uniaxial | Scalpel |
| 0304b-4 | Disk | 0.12 | 2.3 | BRP | Uniaxial | Scalpel |
| 0304b-4 | Disk | 0.16 | 2.2 | BRP | Uniaxial | Scalpel |
| 0304b-4 | Strip | 0.31 | 2.4 | BRP | Uniaxial | Scalpel |
| 0304b-5 | Disk | 122 | 68 | Control | Isometric | Scalpel |
| 0304b-5 | Disk | 143 | 82 | Control | Isometric | Scalpel |
| 0304b-5 | Strip | 123 | 76 | Control | Isometric | Scalpel |
| 0304b-7 | Disk | 0.18 | 1.9 | BRP | Isometric | Scalpel |
| 0304b-7 | Disk | 0.15 | 2.1 | BRP | Isometric | Scalpel |
| 0304b-7 | Strip | 1.3 | 8.2 | BRP | Isometric | Scalpel |
| 0304b-6 | Disk | 115 | 76 | Control | Isometric | Scalpel |
| 0304b-6 | Strip | 108 | 71 | Control | Isometric | Scalpel |
| 0304b-8 | Disk | 0.79 | 1.7 | BRP | Isometric | Scalpel |
| 0304b-8 | Strip | 0.19 | 2.9 | BRP | Isometric | Scalpel |

| | Calcium | Phosphorus |
|---|---|---|
| Glut Only Average - Control (µg/mg) | 117.00 | 63.56 |
| Glut Only StDev | 21.80 | 16.79 |
| BRP Process (Uniaxial & Isometric) Average (µg/mg) | 0.41 | 2.90 |
| BRP Process (Uniaxial & Isometric) StDev | 0.38 | 1.80 |

While embodiments of the present invention have been shown and described, various modifications may be made without departing from the scope of the present invention. The invention, therefore, should not be limited, except to the following claims, and their equivalents.

We claim:

1. A method for processing fixed biological tissue to remove phospholipids comprising the steps of:
   (a) immersing the fixed biological tissue in a first fresh bioburden reduction process (BRP) solution, wherein the phospholipids are soluble in the first BRP solution, and wherein the first BRP solution consists essentially of purified water, glutaraldehyde, polysorbate-80, and a buffer to maintain a pH within the range of about 7.3 to 7.5 during processing;
   (b) heating the first fresh BRP solution to a temperature of about 37° C. to remove phospholipids from the tissue;
   (c) removing the fixed biological tissue from the fresh BRP solution;
   (d) immediately immersing the fixed biological tissue in a next fresh BRP solution having a composition substantially the same as the first fresh BRP solution; and
   (e) heating the next fresh BRP solution to a temperature of about 37° C. to remove phospholipids from the tissue to mitigate or reduce calcification of the tissue.

2. The method of claim 1, further comprising the steps of repeating steps (c), (d), and (e) one or more times.

3. The method of claim 1, wherein, in steps (b) and (e), the BRP solution is heated for a period of time between four and sixteen hours.

4. The method of claim 1, wherein the total time the fixed tissue is exposed to BRP solution is no more than about twenty-four hours.

5. A method for processing fixed biological tissue to remove phospholipids comprising the steps of:
   immersing the fixed biological tissue using a co-current, cross-current, or counter-current separation system comprising a fresh bioburden reduction process (BRP) solution, the BRP solution consisting essentially of purified water, glutaraldehyde, polysorbate-80, and a buffer to maintain a pH within the range of about 7.3 to 7.5 during processing; and
   heating the fresh BRP solution to a temperature of about 37° C. to substantially continuously remove phospholipids from the tissue to mitigate or reduce calcification of the tissue.

6. The method of claim 5, wherein the immersion takes place in a co-current separation system.

7. The method of claim 5, wherein the immersion takes place in a cross-current separation system.

8. The method of claim 5, wherein the immersion takes place in a counter-current separation system.

9. The method of claim 1, wherein the fixed biological tissue comprises a leaflet attached to a frame.

10. The method of claim 9, wherein the fixed biological tissue further comprises fabric covering at least a portion of the frame.

11. The method of claim 9, further comprising:
   rinsing the fixed biological tissue; and
   assembling the frame to a valve frame.

12. The method of claim 1, further comprising cutting the fixed biological tissue into leaflets before steps (a)-(e).

13. The method of claim 1, wherein the fixed biological tissue is fixed before steps (a)-(e) by a process comprising:
   cutting biological tissue into strips;
   immersing the strips in fixation solution by one end of the strips with a weight on a lower end of the strips to subject the biological tissue to uniaxial fixation.

14. A method for processing fixed biological tissue using a bioburden reduction process (BRP) solution comprising glutaraldehyde and polysorbate-80 to remove phospholipids, the method comprising:
   (a) attaching the fixed biological tissue to a laminate or frame;
   (b) covering the laminate or frame at least partially with fabric to create a leaflet sub-assembly;
   (c) immersing the leaflet sub-assembly in a first container of the BRP solution, the BRP solution consisting essentially of purified water, glutaraldehyde, polysorbate-80, and a buffer to maintain a pH within the range of about 7.3 to 7.5 during processing;
   (d) heating the first container to a temperature of about 37° C. for a period of time between about four and sixteen (4-16) hours to remove phospholipids from the tissue using the BRP solution;
   (e) removing the leaflet sub-assembly from the first container;
   (f) immediately immersing the leaflet sub-assembly in a second container of the BRP solution; and
   (g) heating the second container to a temperature of about 37° C. to remove phospholipids from the tissue using the BRP solution,
   wherein the total time the tissue is exposed to the BRP solution is no more than about twenty-four hours to mitigate or reduce calcification of the tissue.

15. The method of claim 14, further comprising:
   rinsing the leaflet sub-assembly; and
   assembling the leaflet sub-assembly to a valve frame.

16. The method of claim 14, further comprising cutting the fixed biological tissue into a plurality of leaflets, wherein each of the leaflets are processed using steps (a)-(g).

17. The method of claim 14, further comprising:
   removing the leaflet sub-assembly from the second container;
   immediately immersing the leaflet sub-assembly in a third container of the BRP solution.

18. The method of claim 14, wherein the first container is reused as the second container.

19. The method of claim 1, wherein the buffer comprises sodium chloride, potassium phosphate monobasic, sodium phosphate dibasic heptahydrate, and one or both of hydrochloric acid and sodium hydroxide as needed to maintain the pH within the range of about 7.3 to 7.5 during processing.

20. The method of claim 1, wherein the buffer consists essentially of sodium chloride, potassium phosphate monobasic, sodium phosphate dibasic heptahydrate, and one or both of hydrochloric acid and sodium hydroxide as needed to maintain the pH within the range of about 7.3 to 7.5 during processing.

21. The method of claim 5, wherein the buffer comprises sodium chloride, potassium phosphate monobasic, sodium phosphate dibasic heptahydrate, and one or both of hydrochloric acid and sodium hydroxide as needed to maintain the pH within the range of about 7.3 to 7.5 during processing.

22. The method of claim 5, wherein the buffer consists essentially of sodium chloride, potassium phosphate monobasic, sodium phosphate dibasic heptahydrate, and one or both of hydrochloric acid and sodium hydroxide as needed to maintain the pH within the range of about 7.3 to 7.5 during processing.

23. The method of claim 14, wherein the buffer comprises sodium chloride, potassium phosphate monobasic, sodium phosphate dibasic heptahydrate, and one or both of hydrochloric acid and sodium hydroxide as needed to maintain the pH within the range of about 7.3 to 7.5 during processing.

24. The method of claim 14, wherein the buffer consists essentially of sodium chloride, potassium phosphate monobasic, sodium phosphate dibasic heptahydrate, and one or both of hydrochloric acid and sodium hydroxide as needed to maintain the pH within the range of about 7.3 to 7.5 during processing.

* * * * *